United States Patent [19]

Hafner et al.

[11] Patent Number: 4,710,316

[45] Date of Patent: Dec. 1, 1987

[54] ALDEHYDES, ACETALS, ALCOHOLS AND ETHERS HAVING 3-METHYL- OR 3,5-DIMETHYL-BENZYL GROUPS, THEIR MANUFACTURE AND PERFUME MATERIALS CONTAINING SAME

[75] Inventors: Walter Hafner, Eurasburg; Peter Ritter, Kempten; Helmut Gebauer; Marlies Regiert, both of Munich, all of Fed. Rep. of Germany

[73] Assignee: Consortium fur Elektrochemische Industrie GmbH, Munich, Fed. Rep. of Germany

[21] Appl. No.: 896,019

[22] Filed: Aug. 13, 1986

[30] Foreign Application Priority Data

Sep. 4, 1985 [DE] Fed. Rep. of Germany ....... 3531585

[51] Int. Cl.$^4$ ...................... A61K 7/46; A61K 31/13; A61K 43/164; A61K 47/105
[52] U.S. Cl. ...................... 512/20; 568/458; 568/465; 568/658; 568/826; 568/846; 512/21
[58] Field of Search ............ 252/522 R; 568/458, 568/465, 826, 846, 658

[56] References Cited

U.S. PATENT DOCUMENTS

| | | | |
|---|---|---|---|
| 4,362,657 | 12/1982 | Kiwala et al. | 252/522 R |
| 4,492,645 | 1/1985 | Sprecker | 252/522 R |
| 4,549,983 | 10/1985 | Wiegers et al. | 252/522 R |

OTHER PUBLICATIONS

Kropf et al., "Chemical Abstracts" vol. 76(1):3499.
Kokai, "Chemical Abstracts" vol. 99(15):117871v.

Primary Examiner—Werren B. Lone
Attorney, Agent, or Firm—Collard, Roe & Galgano

[57] ABSTRACT

Compounds of the general formula (I)

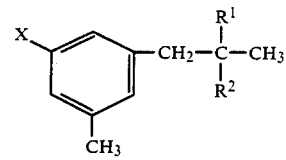

and compounds of the general formula (II)

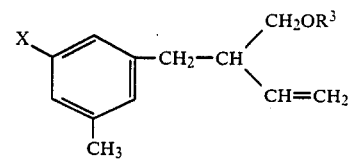

in which
$R^1$ represents —OH, —CH$_2$OH, —CH$_2$—OCH$_3$, —CHOH—CH$_3$, —CHO or —CH(OCH$_3$)$_2$,
$R^2$ represents methyl or ethyl,
$R^3$ represents hydrogen or methyl, and
X represents hydrogen or methyl, are disclosed.

Processes for the manufacture of certain compounds of formula (I) and for those of formula (II) are also provided. The compounds are useful as perfume materials.

3 Claims, No Drawings

ALDEHYDES, ACETALS, ALCOHOLS AND ETHERS HAVING 3-METHYL- OR 3,5-DIMETHYL-BENZYL GROUPS, THEIR MANUFACTURE AND PERFUME MATERIALS CONTAINING SAME

This invention relates to a selection of aldehydes, acetals derived therefrom, alcohols and ethers derived therefrom, having 3-methyl- or 3.5-dimethyl-benzyl substituents.

According to Chemikerzeitung 97 (1973), No. 1, page 8 ff., benzyldimethyl carbinol is known as a perfume material having a flowery note.

It has now been found that a selection of 3-methyl- and 3,5-dimethyl-benzyl compounds are distinguished from an analogous selection of unsubstituted compounds by improved perfume quality: the secondary notes that impair the natural fragrance are reduced; the fragrance spectrum is condensed to give a natural note which is then all the more intense.

The subject of the present invention concerns compounds of the general formula (I)

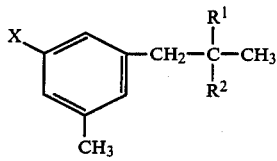

and compounds of the formula (II)

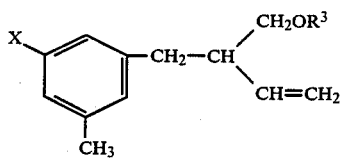

in which
$R^1$ represents —OH, —CH$_2$OH, —CH$_2$—OCH$_3$, —CHOH—CH$_3$, —CHO and —CH(OCH$_3$)$_2$,
$R^2$ represents methyl or ethyl,
$R^3$ represents hydrogen or methyl, and
X represents hydrogen or methyl.

Examples of compounds according to the invention are:
2-(3-methylbenzyl)-3-buten-1-ol
2-(3,5-dimethylbenzyl)-3-buten-1-ol
1-methoxy-2-(3-methylbenzyl)-3-butene
1-methoxy-2-(3,5-dimethylbenzyl)-3-butene
2,2-dimethyl-3-(3-methylphenyl)-propan-1-ol
2,2-dimethyl-3-(3,5-dimethylphenyl)-propan-1-ol
2-methyl-2-(3-methylbenzyl)-butan-1-ol
2-methyl-2-(3,5-dimethylbenzyl)-butan-1-ol
2-(3-methylbenzyl)-propan-2-ol
2-(3,5-dimethylbenzyl)-propan-2-ol
2-(3-methylbenzyl)-butan-2-ol
2-(3,5-dimethylbenzyl)-butan-2-ol
2,2-dimethyl-3-(3-methylphenyl)-propionaldehyde
2,2-dimethyl-3-(3,5-dimethylphenyl)-propionaldehyde
2-methyl-2-(3-methylbenzyl)-butyraldehyde
2-methyl-2-(3,5-dimethylbenzyl)-butyraldehyde
1,1-dimethoxy-2,2-dimethyl-3-(3-methylphenyl)-propane
1,1-dimethoxy-2,2-dimethyl-3-(3,5-dimethylphenyl)-propane
1,1-dimethoxy-2,2-dimethyl-3-(3-methylphenyl)-butane
1,1-dimethoxy-2,2-dimethyl-3-(3,5-dimethylphenyl)-butane
3-methyl-3-(3-methylbenzyl)-butan-2-ol
3-methyl-3-(3,5-dimethylbenzyl)-butan-2-ol
3-methyl-3-(3-methylbenzyl)-pentan-2-ol
3-methyl-3-(3,5-dimethylbenzyl)-pentan-2-ol
1-methoxy-2,2-dimethyl-3-(3-methylphenyl)-propane
1-methoxy-2,2-dimethyl-3-(3,5-dimethylphenyl)-propane.

The compounds of the formula II can be obtained from butadienemagnesium and the corresponding benzyl chlorides by subsequent oxidation followed by hydrolysis. The free OH group is then optionally etherified in a further reaction stage The process is characterized in that
(a) benzyl chloride of the formula

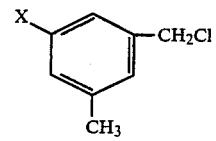

in which X represents hydrogen or methyl is reacted with butadienemagnesium,
(b) the reaction product according to (a) is oxidized
(c) the oxidation product according to (b) is subjected to acidic hydrolysis, and
(d) the reaction product according to (c) is optionally methylated at the free OH group.

The reaction is illustrated by the following equation:

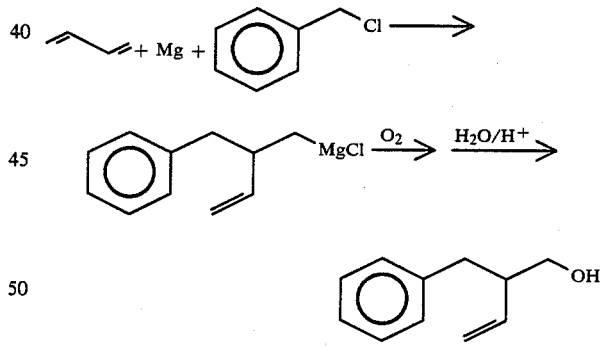

Butadienemagnesium can be obtained in a conventional manner from metallic magnesium and butadiene. Solvents, such as, for example, tetrahydrofuran, inter alia, are generally used.

The benzyl chlorides used as starting substances are likewise known substances. The reaction of the aforesaid starting compounds is advantageously carried out at temperatures of from 0° C. to 65° C. The oxidation of the resulting magnesium chloride is best carried out with oxygen or oxygen-containing gases, especially air. The oxidation temperatures are normally from −25° C. to 30° C.

The hydrolysis of the oxidation product is best carried out in the presence of mineral acids, such as hydrochloric acid, sulfuric acid and the like.

The optional etherification of the free OH group is carried out according to conventionally known methods, for example, the alcohol is converted into the alcoholate and then reacted with methylating agents, such as dimethyl sulfate and the like, to form the corresponding ether.

Insofar as R¹ represents a carbon-containing radical, the compounds of the formula (I) can be obtained by condensing the corresponding benzyl chlorides with isobutyraldehyde or with 2-methylbutyraldehyde and, optionally, further derivatizing the resulting aldehydes.

The process for the manufacture of the compounds of the formula

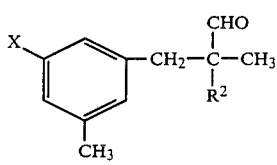

in which
R² represents methyl or ethyl, and
X represents hydrogen or methyl,
is characterized in that benzyl chlorides of the formula

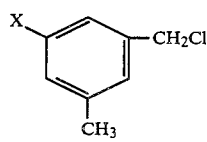

are condensed with isobutyraldehyde or 2-methylbutyraldehyde in an organic/alkaline two-phase system, optionally in the presence of phase transfer catalysts.

The benzyl chloride and the aldehyde are used in approximately equimolar amounts. The organic/alkaline two-phase system is formed from an organic water-immiscible inert solvent and a 5 to 50% by weight aqueous solution or alkali metal hydroxide in solid form.

As phase transfer catalysts, useful are, for example, crown ethers or quaternary ammonium and phosphonium salts, in amounts of from 0.5 to 5 mole-%, calculated on benzyl chloride.

The reaction temperatures are from 20° C. to 150° C., especially from 60° C. to 70° C.

The process is advantageously carried out so that the two-phase system and the catalyst are taken first and a mixture of the reactants is added dropwise thereto.

The corresponding primary alcohols can be obtained from the resulting aldehydes by reducing methods known in the art. The secondary alcohols are manufactured by reacting the aldehydes with methyl Grignard reagents. The ethers can be obtained by methylating the primary alcohols according to etherification processes known in the art. The acetals can, likewise, be obtained from the aldehydes according to the processes of the prior art.

The tertiary alcohols of the formula

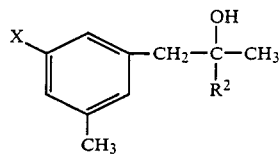

according to the invention are ultimately obtained by reacting 3-methyl- or 3,5-dimethyl-benzylmagnesium chloride with acetone or with methyl ethyl ketone.

The reaction is shown by way of example by the following equation:

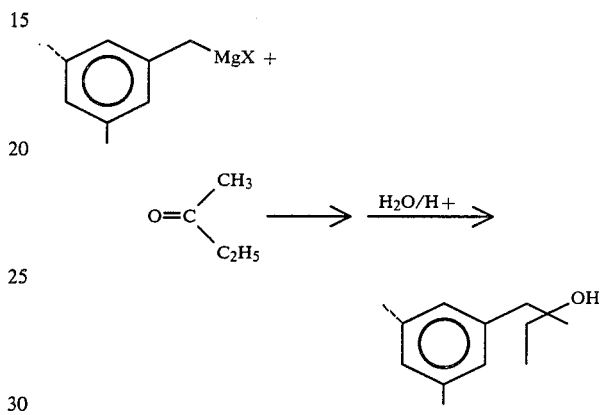

The preferred process for the manufacture of compounds of the formula

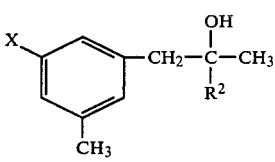

in which
R² represents methyl or ethyl, and
X represents hydrogen or methyl,
is characterized in that benzylmagnesium chloride of the formula

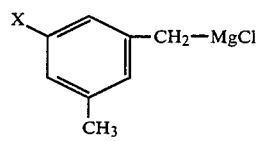

is reacted with acetone or methyl ethyl ketone.

The benzylmagnesium chlorides can be obtained according to processes known to the skilled artisan for the manufacture of Grignard reagents from the corresponding benzyl chlorides and metallic magnesium. The operation is carried out, generally, in anhydrous solvents, such as, for example, diethyl ether. The reaction temperatures are generally from 0° C. to 65° C. The subsequent acidic hydrolysis yields the free alcohol. For details, reference should be made to the following examples.

The compounds according to the invention are used as perfume materials. They are useful for perfuming cosmetic and industrial products. Flowery notes, for example, the note of lily of the valley, magnolia, roses, cyclamen, inter alia, predominate.

The invention will now be more fully described by the following examples. It should, however, be noted that such examples are given by way of illustration and not of limitation.

EXAMPLE 1

Manufacture of 2-(3,5-dimethylbenzyl)-3-buten-1-ol 27 g of pulverulent metallic magnesium were placed in a 2 liter four-necked flask having a thermometer, a stirrer, a dropping funnel with a gas inlet attachment and a reflux condenser. The flask was flushed with butadiene and the magnesium powder was covered with a layer of dry tetrahydrofuran. In order to start the reaction, 2 ml of ethyl bromide were added and the reaction mixture was heated to 55° C. While constantly introducing butadiene, a total of 400 ml of tetrahydrofuran was then added. When the reaction mixture had turned greenish-yellow, 155 g of 3,5-dimethyl-benzyl chloride and 200 ml of tetrahydrofuran were metered in. The metering speed was regulated so that the already mentioned greenish-yellow color of the reaction mixture was constantly maintained. The supply of butadiene was always in accordance with the consumption. The consumption was monitored by means of an elastic storage container which was mounted on the reflux condenser. After 3 hours, the metallic magnesium had dissolved and the first reaction stage was completed.

The flask was afterwards flushed with argon and then the reaction mixture was cooled to a temperature of 0° C. Dry $CO_2$-free air was then introduced in order to effect oxidation. The airstream was regulated so that the temperature did not rise above 10° C.

For the purpose of hydrolysis, the contents of the flask were then poured onto ice, while stirring, and acidified with concentrated hydrochloric acid. The phases were separated, the organic phase was extracted by shaking three times with water and once with potassium carbonate solution and finally dried with solid potassium carbonate. Distillation was carried out using a Vigreux column 30 cm long. After distilling off the solvents, 78 g of (3,5-dimethylbenzyl)-butenols, of which 2-(3,5-dimethylbenzyl)-3-buten-1-ol, with 70%, formed the main constituent, were obtained in a temperature range of from 80° C. to 85° C. at 0.12 mbar.

Fragrance: green and flowery, rose with a geranium note.

EXAMPLE 2

Manufacture of 2-(3-methylbenzyl)-3-buten-1-ol

The method according to Example 1 was repeated, except that 3-methylbenzyl chloride was used instead of 3,5-dimethylbenzyl chloride.

Ingredients:
35 g of magnesium powder
197 g of 3-methylbenzyl chloride 114 g of a 5:1 isomeric mixture of 2-(3-methylbenzyl)-3-buten-1-ol (as the main constituent) and 1(3-methylphenyl)-4-penten-2-ol were obtained by fractional distillation at 0.13 mbar in a temperature range of from 84° C. to 86° C.

Fragrance: flowery, fruity, green, reminiscent of pears.

EXAMPLE 3

Manufacture of 2,2-dimethyl-3-(3-methylphenyl)-propionaldehyde

A pre-mix of 23.3 g of NaOH, 2.5 g of tetrabutylammonium iodide, 107 ml of water, 25 ml of toluene and 9 ml of tetrahydrofuran under argon was heated to 70° C. A mixture of 70 g (0.5 moles) of 3-methylbenzyl chloride and 50.4 g (0.7 moles) of isobutyraldehyde was added dropwise to this pre-mix within a period of 2 hours while stirring vigorously. The reaction mixture was then maintained at a temperature of 75° C. for 3 hours. After separating the phases and removing the solvents, 66.5 g of end product were obtained by fractional distillation at 0.12 mbar in a temperature range of from 50° C. to 52° C.

Fragrance: green, reminiscent of leaves, with flowery-aldehydic aspects

EXAMPLE 4

Manufacture of 3-methyl-(3-methylbenzyl)-butan-2-ol

A solution of 10 g of methylmagnesium chloride in 100 ml of tetrahydrofuran was added at a temperature of from 25° C. to 30° C., and with the exclusion of air, to 17 g of 2,2-dimethyl-3-(3-methylphenyl)-propionaldehyde (according to Example 3). After 5 hours at 30° C., the reaction mixture was poured onto ice and acidified with hydrochloric acid. The phases were then separated and the organic phase was washed with 100 ml of water and 100 ml of sodium bicarbonate solution. Finally, drying was carried out with solid potassium carbonate. Fractional distillation yielded 15 g of end product at 0.12 mbar in a temperature range of from 79° C. to 82° C.

Fragrance: perfume of lily of the valley, flowery.

EXAMPLE 5

Manufacture of 2,2-dimethyl-3-(3-methylphenyl)-propan-1-ol 44 g of 2,2-dimethyl-3-(3-methylphenyl)-propionaldehyde (according to Example 3) were added in small portions under argon and at 20° C. to a pre-mix of 150 ml of isopropanol and 3.8 g of sodium borohydride. The entire mixture was stirred for 24 hours at 20° C. Excess sodium borohydride was then decomposed by the dropwise addition of 2N HCl. The reaction mixture was then taken up in 150 ml of diethyl ether and extracted with water, 2N NaOH and, again, with water.

After drying over potassium carbonate, distillation was carried out using a packed column 30 cm long. 30 g of end product were obtained at 0.12 mbar in a temperature range of from 70° C. to 72° C.

Fragrance: fresh, soft, slightly green flowery perfume, reminiscent of lime blossom and lily of the valley with a citrus note.

EXAMPLE 6

Manufacture of 1-methoxy-2,2-dimethyl-3-(3-methylphenyl)-propane

In a 250 ml three-necked flask flushed with argon, 4.5 g of 2,2-dimethyl-3-(3-methylphenyl)-propan-1-ol (according to Example 5) in 50 ml of dry tetrahydrofuran were boiled for 1½ hours under reflux with 0.7 g of sodium hydride. 3.2 g of dimethyl sulfate in 30 ml of tetrahydrofuran were then added dropwise thereto and the mixture was boiled under reflux for a further hour.

After leaving the reaction mixture to stand for 24 hours, it was extracted by shaking with 20 ml of 10% by weight sodium hydroxide solution. Finally, the organic phase was dried with potassium carbonate and subjected to fractional distillation. 3.6 g of end product were obtained at 52° C./0.12 mbar.

Fragrance: spicy/flowery with a fresh headnote.

EXAMPLE 7

Analogously to Example 6, 17.6 g of 2-(3-methylbenzyl)-3-buten-1-ol (according to Example 2) in 80 ml of tetrahydrofuran were reacted with 2.6 g of sodium hydride and the resulting alcoholate was reacted with 12.6 g of dimethyl sulfate in 100 ml of tetrahydrofuran.

Fractional distillation at 60° C./0.25 mbar yielded 10 g of end product.

Fragrance: sweet, woody, slightly flowery, green.

EXAMPLE 8

Manufacture of 2,2-dimethyl-3-(3,5-dimethylphenyl)-propionaldehyde

A pre-mix of 125 g of 30% by weight sodium hydroxide solution, 5 g of potassium iodide, 10 g of tetradecyltrimethylammonium bromide, 200 ml of tetrahydrofuran and 200 ml of toluene was heated to 75° C. A mixture of 155 g of 3,5-dimethylbenzyl chloride, 110 g of isobutyraldehyde, 50 ml of tetrahydrofuran and 50 ml of toluene was added dropwise to this pre-mix while stirring vigorously. The entire mixture was then boiled under reflux for 6 hours. The phases were then separated and the organic phase was first washed with warm water and then filtered with the addition of activated carbon. Finally, distillation was carried out using a packed column with wire spirals. The distillation, carried out in a temperature range of from 72° C. to 74° C. at 0.25 mbar, yielded 106 g of 92% 2,2-dimethyl-3-(3,5-dimethylphenyl)-propionaldehyde.

Fragrance: green note, slightly flowery, aldehydic, spicy, slightly reminiscent of safrole.

EXAMPLE 9

Manufacture of 2,2-dimethyl-3-(3,5-dimethylphenyl)-propan-1-ol 20 g of 2,2-dimethyl-3-(3,5-dimethylphenyl)-propionaldehyde were added dropwise, in a temperature range of from 30° C. to 35° C., to a pre-mix, flushed with argon, of 3 g of sodium borohydride in 100 ml of isopropanol in a 500 ml four-necked flask. After 2 hours, the temperature of the reaction mixture was increased to 60° C. for 1 hour. Excess sodium borohydride was then decomposed by adding 2N hydrochloric acid. The main quantity of isopropanol was then distilled off and the residue was taken up in 100 ml of ether. Extraction was then carried out with 2N NaOH and water and the organic phase was dried with potassium carbonate. Fractional distillation in a temperature range of from 81° C. to 83° C. at 0.12 mbar yielded 9 g of end product.

Fragrance: perfume of white blossom, lily of the valley, magnolia, tuberose, also somewhat ambered.

EXAMPLE 10

Manufacture of 2-(3,5-dimethylbenzyl)-butan-2-ol 3,5-dimethylbenzylmagnesium chloride was manufactured from 2.6 g of magnesium powder and 15.5 g of 3,5-dimethylbenzyl chloride dissolved in 200 ml of diethyl ether and reacted with 7.5 g of methyl ethyl ketone in a temperature range of from 20° C. to 25° C. After 2 hours, the whole was poured onto ice and acidified, and the organic phase was separated off and extracted by shaking with water and sodium bicarbonate solution. After drying the organic phase with solid potassium carbonate, fractional distillation was carried out. 13 g of end product were obtained in a temperature range of from 63° C. to 65° C. at 0.12 mbar.

Fragrance: green, reminiscent of cyclamen and lily of the valley, with a green note of leaves.

EXAMPLE 11

Manufacture of 2-methyl-2-(3-methylbenzyl)-butyraldehyde 300 ml of toluene, 70 g of 30% by weight sodium hydroxide solution, 3.3 g of potassium iodide and 6.7 g of tetradecyltrimethylammonium bromide were placed in a 1 liter three-necked flask. A mixture of 70 g of 3-methylbenzyl chloride, 50 ml of 2-methylbutyraldehyde and 100 ml of toluene was added dropwise to this pre-mix at 85° C. within a period of ½ hour. The reaction mixture was then stirred for 4 hours at 85° C. After separating the phases, the organic phase was washed several times with water and filtered over activated carbon. Finally, fractional distillation was carried out. 40 g of a product with a 93% content of end product were obtained at 63° C./0.06 mbar.

Fragrance: green note with a flowery ozone character, slightly spicy.

EXAMPLE 12

Manufacture of 2-methyl-2-(3-methylbenzyl)-butan-1-ol 29 g of 2-methyl-2-(3-methylbenzyl)-butyraldehyde (according to Example 11) were stirred for 20 hours at room temperature with 3 g of sodium borohydride in 80 ml of ethanol. Excess sodium borohydride was then decomposed with 2N HCl. After removing the ethanol, the residue was taken up in ether and extracted with water. The organic phase was extracted by shaking with 2N NaOH and water and dried with solid potassium carbonate. After removing the solvent, fractional distillation was carried out. 20 g of end product were obtained in a temperature range of from 72° C. to 73° C. at 0.12 mbar.

Fragrance: fresh flowery note, slightly fruity, woody.

While only several embodiments and examples of the present invention have been shown and described, it is obvious that many changes and modifications may be made thereunto, without departing from the spirit and scope of the invention.

What is claimed is:

1. A compound selected from the group consisting of a compound of formula (I)

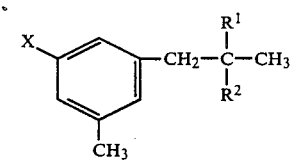

and a compound of formula (II)

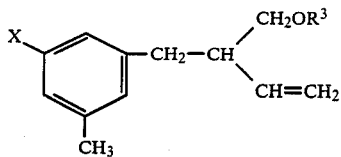

wherein
R[1] is a substituent selected from the group consisting of —OH, —CH₂OH, —CH₂—OCH₃, —CHOH—CH₃, —CHO and —CH(OCH₃)₂,
R[2] is methyl or ethyl,
R[3] is hydrogen or methyl,
X is hydrogen or methyl,
and wherein 2-methyl-3-(3-methylphenyl)-propan-2-ol and 2-methyl-3-(3,5-dimethylphenyl)-propon-2-ol are excluded.

2. A perfume material containing the compound of claim 1.

3. A compound according to claim 1 selected from the group consisting of:
2-(3-methylbenzyl)-3-buten-1-ol,
2(3,5-dimethylbenzyl)-3-buten-1-ol,
1-methoxy-2-(3-methylbenzyl)-3-butene,
1-methoxy-2-(3,5-dimethylbenzyl)-3-butene,
2,2-dimethyl-3-(3-methylphenyl)-propan-1-ol,
2,2-dimethyl-3-(3,5-dimethylphenyl)-propan-1-ol,
2-methyl-2-(3-methylbenzyl)-butan-1-ol,
2-methyl-2-(3,5-dimethylbenzyl)-butan-1-ol,
2-(3-methylbenzyl)-propan-2-ol,
2-(3,5-dimethylbenzyl)-propan-2-ol,
2-(3-methylbenzyl)-butan-2-ol,
2-(3,5-dimethylbenzyl)-butan-2-ol,
2,2-dimethyl-3-(3-methylphenyl)-propionaldehyde,
2,2-dimethyl-3-(3,5-dimethylphenyl)-propionaldehyde,
2-methyl-2-(3-methylbenzyl)-butyraldehyde,
2-methyl-2-(3,5-dimethylbenzyl)-butyraldehyde,
1,1-dimethoxy-2,2-dimethyl-3-(3-methylphenyl)-propane,
1,1-dimethoxy-2,2-dimethyl-3-(3,5-dimethylphenyl)-propane,
1,1-dimethoxy-2,2-dimethyl-3-(3-methylphenyl)-butene,
1,1-dimethoxy-2,2-dimethyl-3-(3,5-dimethylphenyl)-butane,
3-methyl-3-(3-methylbenzyl)-butan-2-ol,
3-methyl-3-(3,5-dimethylbenzyl)-butan-2-ol,
3-methyl-3-(3-methylbenzyl)-pentan-2-ol,
3-methyl-3-(3,5-dimethylbenzyl)-pentan-2-ol,
1-methoxy-2,2-dimethyl-3-(3-methylphenyl)-propane, and
1-methoxy-2,2-dimethyl-3-(3,5-dimethylphenyl)-propane.

* * * * *